US011311709B2

(12) United States Patent
Mansour et al.

(10) Patent No.: US 11,311,709 B2
(45) Date of Patent: *Apr. 26, 2022

(54) CLOSED MALE LUER DEVICE FOR USE WITH NEEDLELESS ACCESS DEVICES (71) Applicant: CAREFUSION 303, INC., San Diego, CA (US)

(72) Inventors: George M. Mansour, Pomona, CA (US); Soon Park, Cypress, CA (US); Jonathan Yeh, Diamond Bar, CA (US)

(73) Assignee: CareFusion 303, Inc., San Diego, CA (US)

( * ) Notice: Subject to any disclaimer, the term of this patent is extended or adjusted under 35 U.S.C. 154(b) by 306 days.

This patent is subject to a terminal disclaimer.

(21) Appl. No.: 15/997,592

(22) Filed: Jun. 4, 2018

(65) Prior Publication Data
US 2018/0280678 A1 Oct. 4, 2018

Related U.S. Application Data (63) Continuation of application No. 14/795,727, filed on Jul. 9, 2015, now Pat. No. 9,987,479.

(51) Int. Cl.
A61M 39/10 (2006.01)
A61M 39/22 (2006.01)
(Continued)

(52) U.S. Cl.
CPC ........ A61M 39/10 (2013.01); A61M 39/1011 (2013.01); A61M 39/22 (2013.01);
(Continued)

(58) Field of Classification Search
CPC .. A61M 39/10; A61M 39/1011; A61M 39/26; A61M 2039/1016;
(Continued)

(56) References Cited

U.S. PATENT DOCUMENTS 4,673,400 A * 6/1987 Martin ................. A61M 39/14
604/536
5,330,450 A * 7/1994 Lopez ................. A61M 39/04
604/284
(Continued)

FOREIGN PATENT DOCUMENTS

CN 101111282 1/2008
EP 1839699 A1 10/2007
(Continued)

OTHER PUBLICATIONS

Extended European Search Report for Application No. 19203247.2, dated Dec. 13, 2019, 8 pages.
(Continued)

Primary Examiner — Nathan R Price
Assistant Examiner — Courtney B Fredrickson
(74) Attorney, Agent, or Firm — Morgan, Lewis & Bockius LLP (57) ABSTRACT A medical connector can include a body having a fluid path with an inlet port, an outlet port, a luer portion, and a post extending through a fluid path. An arm having a latch member is coupled to the body to engage a ridge or thread on an exterior surface of a reciprocal connector. The arm may also include an extension. When the connector is in an open position, the latch member restricts retraction of the reciprocal connector from the outlet port. A seal is coupled to the body and includes a flap extending across the outlet port or a bellows to compress along an axis. In a closed position, the post restricts flow through the luer portion. In an open position, the post permits flow through the luer portion.

17 Claims, 10 Drawing Sheets (51) Int. Cl.
*A61M 39/26* (2006.01)
*A61M 39/24* (2006.01)

(52) U.S. Cl.
CPC ..... *A61M 39/26* (2013.01); *A61M 2039/1016* (2013.01); *A61M 2039/1061* (2013.01); *A61M 2039/1066* (2013.01); *A61M 2039/1072* (2013.01); *A61M 2039/1077* (2013.01); *A61M 2039/244* (2013.01); *A61M 2039/2433* (2013.01); *A61M 2039/261* (2013.01); *A61M 2039/268* (2013.01)

(58) Field of Classification Search
CPC .. A61M 2039/1061; A61M 2039/1072; A61M 2039/1077; A61M 2039/2433; A61M 2039/24; A61M 2039/261
See application file for complete search history.

(56) References Cited

U.S. PATENT DOCUMENTS

| | | | |
|---|---|---|---|
| 5,839,715 | A | 11/1998 | Leinsing |
| 6,875,205 | B2 | 4/2005 | Leinsing |
| 8,241,268 | B2 | 8/2012 | Whitley |
| 8,597,237 | B2 | 12/2013 | Yow et al. |
| 2005/0015075 | A1 | 1/2005 | Wright et al. |
| 2005/0038397 | A1 | 2/2005 | Newton et al. |
| 2005/0087715 | A1 | 4/2005 | Doyle |
| 2005/0090805 | A1 | 4/2005 | Shaw et al. |
| 2010/0174242 | A1 | 7/2010 | Anderson et al. |
| 2010/0179514 | A1 | 7/2010 | Guala |

FOREIGN PATENT DOCUMENTS

| | | | |
|---|---|---|---|
| EP | 2881138 A1 | 6/2015 | |
| FR | 2931363 A1 * | 11/2009 | ............ A61M 39/26 |
| JP | S59177056 A | 10/1984 | |
| JP | H10323397 A | 12/1998 | |
| JP | 2014030489 A | 2/2014 | |
| JP | 2014526315 A | 10/2014 | |
| WO | WO-90005559 | 5/1990 | |
| WO | WO-2005007221 | 1/2005 | |
| WO | WO-2013036854 A1 | 3/2013 | |
| WO | WO-2014163850 | 10/2014 | |

OTHER PUBLICATIONS

"Around." Merriam-Webster.com. Merriam-Webster, n.d. Web. Jul. 6, 2017.
International Search Report and Written Opinion for Application No. PCT/US2016/040999, dated Oct. 12, 2016, 12 pages.
Australia Office Action for Application No. 2016289463, dated Feb. 13, 2020, 3 pages.
Chinese Office Action for Application No. 201610534314.9, dated Mar. 27, 2020, 28 pages.
Japanese Office Action for Application No. 2018-500701, dated Jun. 5, 2020, 14 pages.
Chinese Office Action for Application No. 201610534314.9, dated Feb. 26, 2021, 32 pages including translation.
European Office Action for Application No. 19203247.2, dated Feb. 23, 2021, 4 pages.
Japanese Office Action for Application No. 2018500701, dated Mar. 16, 2021, 4 pages.
Australian Office Action for Application No. 2020286192, dated Aug. 5, 2021, 4 pages.

* cited by examiner

CLOSED MALE LUER DEVICE FOR USE WITH NEEDLELESS ACCESS DEVICES

CROSS REFERENCE TO RELATED APPLICATION

This application claims priority to and is a continuation of U.S. patent application Ser. No. 14/795,727, filed on Jul. 9, 2015, the disclosure of which is incorporated herein by reference in its entirety for all purposes.

BACKGROUND

The present disclosure relates generally to medical connectors used in fluid delivery applications. More specifically, the present disclosure relates to connectors configured to couple with a reciprocal connector via a latch, and to permit flow through the connector when the connector is coupled with a reciprocal connector.

Medical connections are widely used in fluid delivery systems such as those used in connection with intravenous fluid lines, blood access, hemodialysis, peritoneal dialysis, enteral feeding, drug vial access, etc. Many prior art aseptic medical connections have been designed to puncture an elastomeric diaphragm or septum, which has one side in contact with the fluid, with a sharpened hollow hypodermic needle. These connectors have been replaced with luer activated connectors which don't require hypodermic needles, but instead use an activator such as a luer on the end of a syringe or IV line to create a fluid path through a valve in a connector. The removal of the activator causes the valve to close.

SUMMARY

Described herein are needleless connectors with features that help preserve the sterile conditions desirable during and between use of the connectors. An aspect of the present disclosure provides a medical connector comprising: a body having an inlet port, a cavity, an outlet port through a luer portion of the body, a fluid path from the inlet port through the cavity to the outlet port, and an axis between the inlet port and the outlet port; a post extending through the fluid path in the luer portion, wherein when the connector is in a closed position the post restricts flow through the luer portion, and when the connector is in an open position the post permits flow through the luer portion; a seal coupled to the body at the outlet port and configured to extend across the outlet port; and a first arm, pivotably coupled to the body, having a first end and an opposing second end, and a latch member extending from the first end toward the axis; wherein a reciprocal connector having a mating luer is fluidly coupled to the body such that when the connector is in an open position, the latch member restricts retraction of the reciprocal connector from the outlet port.

In some instances, the luer portion of the body is disposed within the mating luer of the reciprocal connector when the connector is in the open position. In some implementations, the latch member comprises a ramp surface, an engagement surface extending transversely to the ramp surface, and an apex area that transitions between the ramp surface and the engagement surface. In some instances, the engagement surface engages at least one of a ridge or thread on an exterior surface of the reciprocal connector. In some embodiments, the first end moves away from the axis when the second end is urged toward the axis. Some embodiments provide the connector and the reciprocal connector are independently rotatable about the axis. In some embodiments, the first arm is pivotable about a point along the axis.

In certain instances of the present disclosure, the seal comprises at least one flap extending from an edge of the outlet port toward the axis. In some instances, a length of the flap from the edge of the outlet port is less than the distance between the edge of the outlet port and the luer portion, such that the flap is free from the luer portion when the flap is displaced into the body. In some embodiments of the present disclosure, the seal comprises a bellows portion circumposed around the axis and configured to compress along the axis.

Certain instances of the present disclosure provide, between the inlet port and the outlet port, at least one of an outer surface of the body and an inner surface of the first arm comprises at least one protrusion that mates with a recess in the other of the outer surface of the body and the first arm. In some embodiments, given an equal application of a force, a moment between the first end and the protrusion is less than a moment between the second end and the protrusion. In certain instances of the present disclosure, an extension is coupled to the first arm between the first end and the protrusion such that when the extension is urged toward the axis, the first end is urged away from the axis. In some instances, at least a portion of the extension extends beyond the axis.

In some implementations, a second arm is pivotably coupled to the body, the second arm having a first end and an opposing second end. In some embodiments, the first end of the first arm and the first end of the second arm move away from the axis when the second end of the first arm and the second end of the second arm are urged toward the axis. In some instances, the second arm comprises a latch member extending from the first end toward the axis. In some embodiments of the present disclosure, the first arm and second arm are pivotably coupled to a bridge, the bridge comprising a slot configured to mate with the protrusion. In some embodiments, a guide portion of the bridge extends to the outlet, the guide portion comprising a ramp surface extending toward the axis and configured to align the connector having a mating luer with the outlet port.

An aspect of the present disclosure provides a medical connector comprising: a body having an inlet port, a cavity, an outlet port through a luer portion of the body, a fluid path from the inlet port through the cavity to the outlet port, and an axis between the inlet port and the outlet port; and a first arm, pivotably coupled to the body, having a first end and an opposing second end, and a latch member extending from the first end toward the axis; wherein when the connector is in a closed position, a seal coupled to the body at the outlet port extends across the outlet port, and when the connector is in an open position, a reciprocal connector having a mating luer extends through the seal. Some instances provide when the connector is in an open position, the reciprocal connector is fluidly coupled to the body. In some embodiments, when the connector is in an open position, the latch member restricts retraction of the reciprocal connector from the outlet port.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

DETAILED DESCRIPTION

In the following detailed description, specific details are set forth to provide an understanding of the subject technology. It will be apparent, however, to one ordinarily skilled in the art that the subject technology may be practiced without some of these specific details. In other instances, well-known structures and techniques have not been shown in detail so as not to obscure the subject technology.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

Figure 1A:
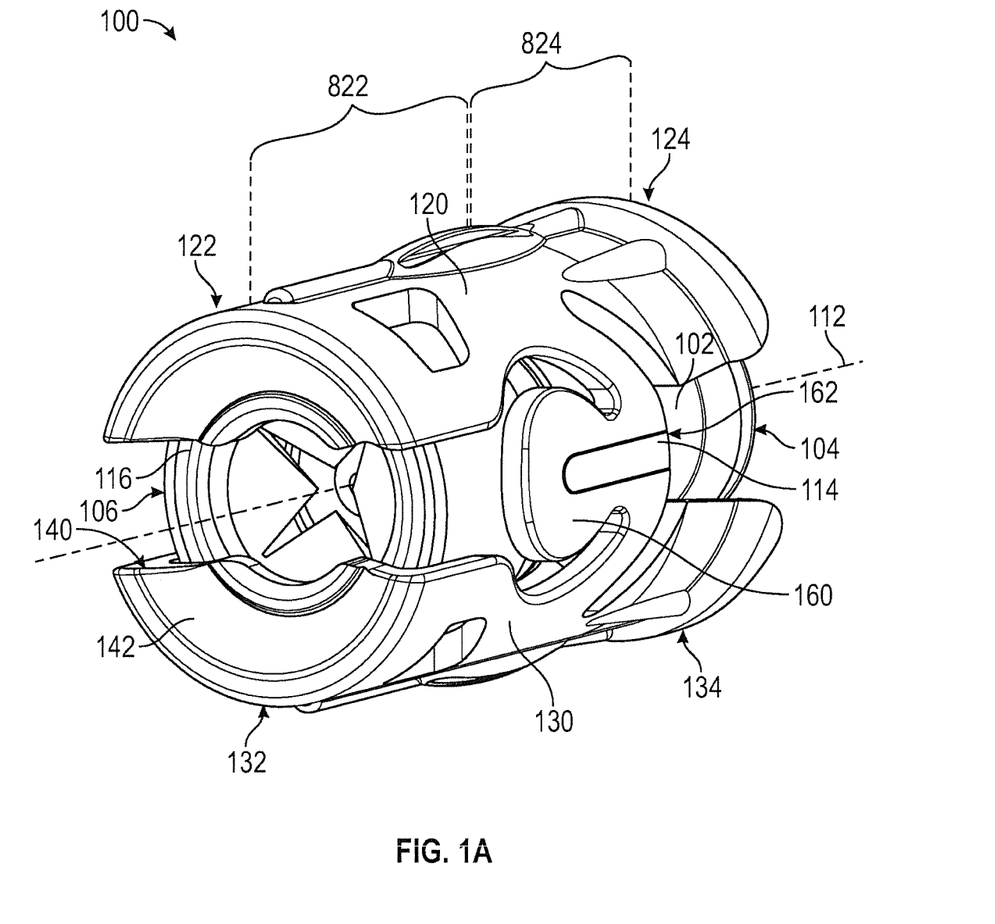
FIG. 1A illustrates a perspective view of an embodiment of a medical connector in accordance with aspects of the present disclosure.
Figure 1B:
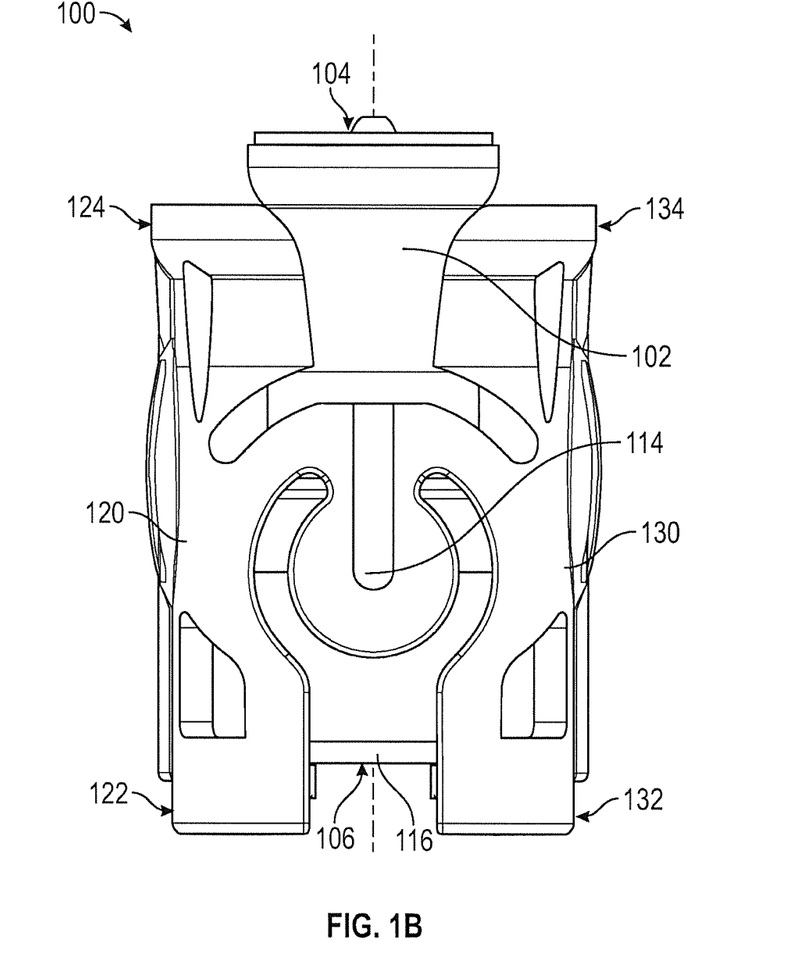
FIG. 1B illustrates an elevation view of the medical connector of FIG. 1A.
Figure 1C:
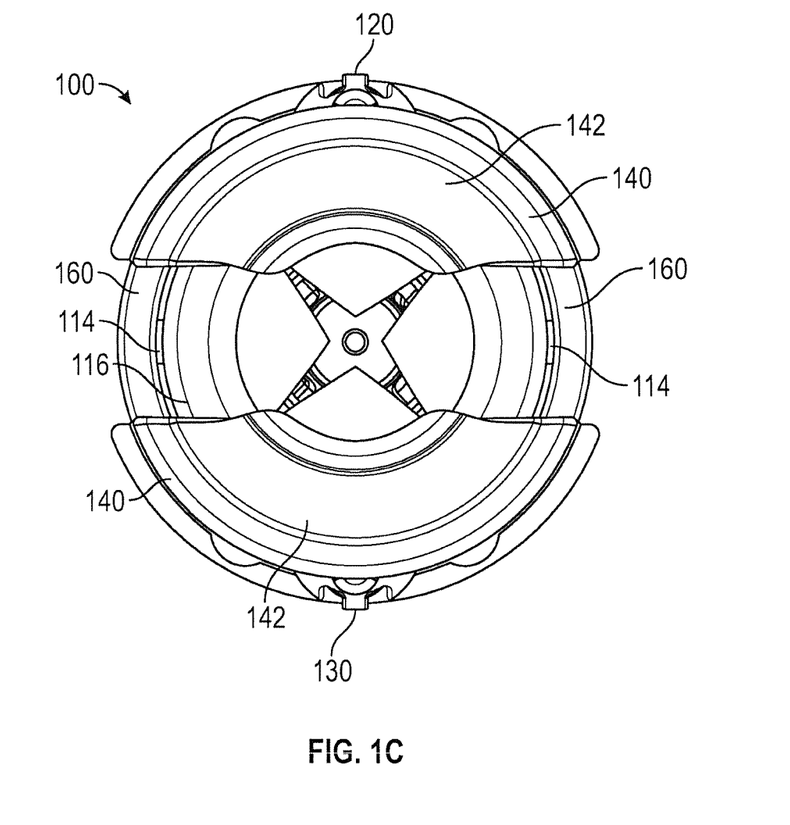
FIG. 1C illustrates a plan view of the medical connector of FIG. 1A.
Figure 2:
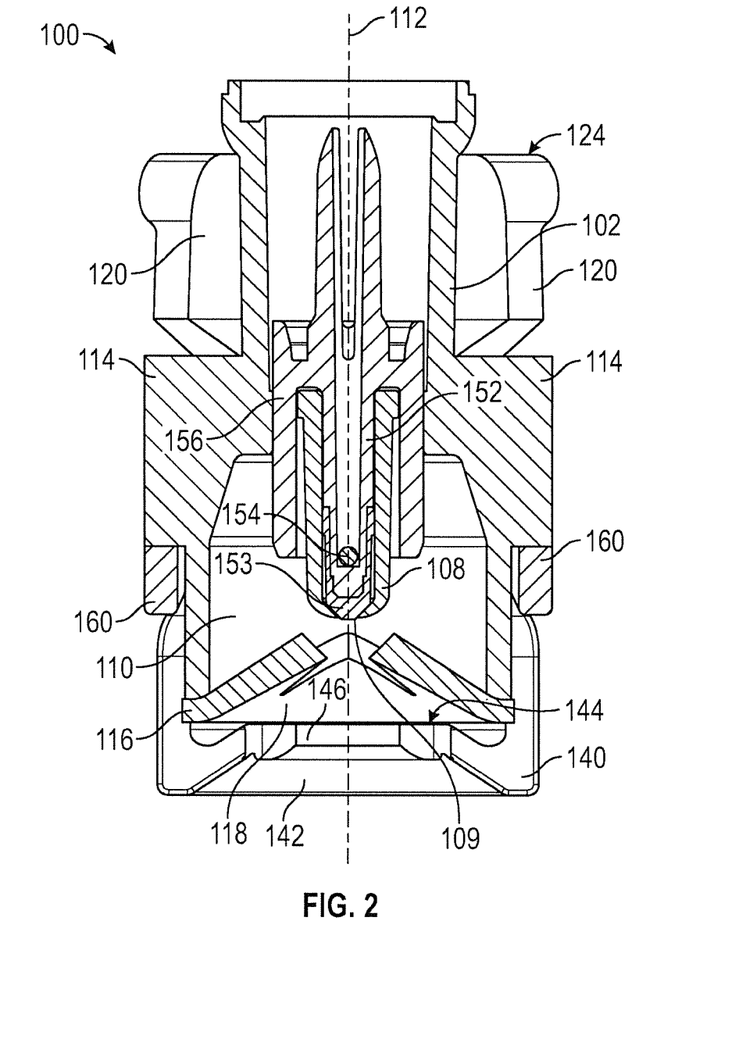
FIG. 2 a sectional view of an embodiment of a medical connector in accordance with aspects of the present disclosure.

As shown in FIGS. 1A-6, embodiments of a medical connector comprise a body having an inlet port, an outlet port, a seal coupled to the body at the outlet port, and a first arm and second arm coupled to the body. Referring to FIGS. 1A-2, an embodiment of a medical connector 100 is illustrated. Medical connector 100 comprises a body 102 having an inlet port 104 and an output port 106. The body 102 defines a cavity 110 and a male luer portion 108 extending toward the outlet port 106 and into the cavity 110. A fluid path between the inlet port 104 and outlet port 106 is defined by the body 102, the male luer portion 108, and cavity 110. Further, an axis 112 is defined between the inlet port 104 and outlet port 106. In an embodiment, a protrusion 114 extends from an exterior surface of the body 102. The protrusion 114 is located between the inlet port 104 and outlet port 106. In some embodiments, the protrusion 114 extends from the body 102 on opposing sides of the axis 112 and includes an elongated tab, groove, ridge, dimple, or aperture.

The first arm 120 comprises a first end 122 and an opposing second end 124. The first arm 120 is coupled to the body 102 coaxially with the axis 112 such that the first end 122 is adjacent to the outlet port 106, and the second end 124 is adjacent to the inlet port 104. The second arm 130 is also coupled to the body 102 coaxially with the axis 112 such that the first end 132 is adjacent to the outlet port 106, and the second end 134 is adjacent to the inlet port 104. Each arm 120 and 130 is shaped as an arch (although other shapes may also be used) around the axis 112 and extends around a portion of the body 102 toward each protrusion 114. In some embodiments, the arms 120 and 130 are unitarily formed with the body 102, for example by machining or casting. In an embodiment, the first arm 120 and the second arm 130 are pivotably coupled to the body 102.

In some embodiments, each arm 120 and 130 is coupled together by a bridge 160 disposed between each arm 120 and 130. In some embodiments, the bridge 160 includes a tab, groove, ridge, dimple, or aperture configured to mate with a protrusion 114 on the body 102. In some embodiments, the bridge 160 defines an elongated slit 162 extending through the bridge partially toward the outlet port 106. The first arm 120 and the second arm 130 are coupled to the body 102 by inserting the body 102 between the first arm 120 and the second arm 130 with the outlet port 106 directed toward the first ends 122 and 132. In this direction, each protrusion 114 enters an elongated slit 162 of a bridge 160 to couple each arm 120 and 132 with the body 102.

In some aspects, the bridge 160 includes a protrusion extending toward the body 102. The protrusion may be configured to mate with a recess in the body 102. The cross-sectional width between a tip of the protrusions extending from each bridge 160 may be less than the cross-sectional width of the outer surface of the body 102. The first arm 120 and the second arm 130 are coupled to the body 102 by inserting the body 102 between the first arm 120 and the second arm 130 with the outlet port 106 directed toward the first ends 122 and 132. As the body 102 is advanced between the protrusions, the bridge 160 between each arm 120 and 130 is biased away from the axis 112.

Once the each protrusion aligns with a respective recess in the body 102, each bridge 160 is permitted to return toward the axis 112 such that the protrusion is received within the recess to couple each arm 120 and 130 with the body 102.

In some embodiments, each arm comprises a first moment 822 between the first end 122 and 132 and a protrusion 114, and a second moment 824 between the second end 124 and 134 and a protrusion 114. In some embodiments, the distance between the first end 122 and 132 and the protrusion 114 is greater than the distance between the second end 124 and 134 and the protrusion 114 such that the first moment 822 is greater than the second moment 824.

Still referring to FIGS. 1A-2, the first end 122 of the first arm 120 and the first end 132 of the second arm 130, each comprise a latch member 140 that extends laterally (or radially) inward from an edge of the first end 122 and 132 toward the axis 112. Each latch member 140 comprises a ramp surface 142, an engagement surface 144, and an apex area 146. Each of the ramp surface 142 and the engagement surface 144 extend transversely to each other. The apex area 146 is disposed at the interface between the ramp surface 142 and the engagement surface 144.

A seal 116 is coupled to the body 102. In an embodiment, the seal 116 is coupled to the outlet port 106 of the body 102 and includes a flap 118 that extends from an edge of the outlet port 106 toward the axis 112. In some embodiments, the seal 116 includes one or more flaps 118 that extend laterally inward from an edge of the outlet port 106. In some embodiments, a seal 116 is coupled to the cavity 110 of the body 102 and includes a bellows portion.

FIG. 2 illustrates a sectional view of an embodiment of the medical connector 100. A post 152 extends through the fluid path in the luer portion 108. The post 152 defines a lumen having an open end, an opposing closed end, and a passage 154 through a sidewall between the open end and the closed end. In some embodiments, the post 152 includes a seal 153 on the outside surface of the closed end to prevent fluid flow through an open tip 109 of the luer portion 108.

Figure 3A:
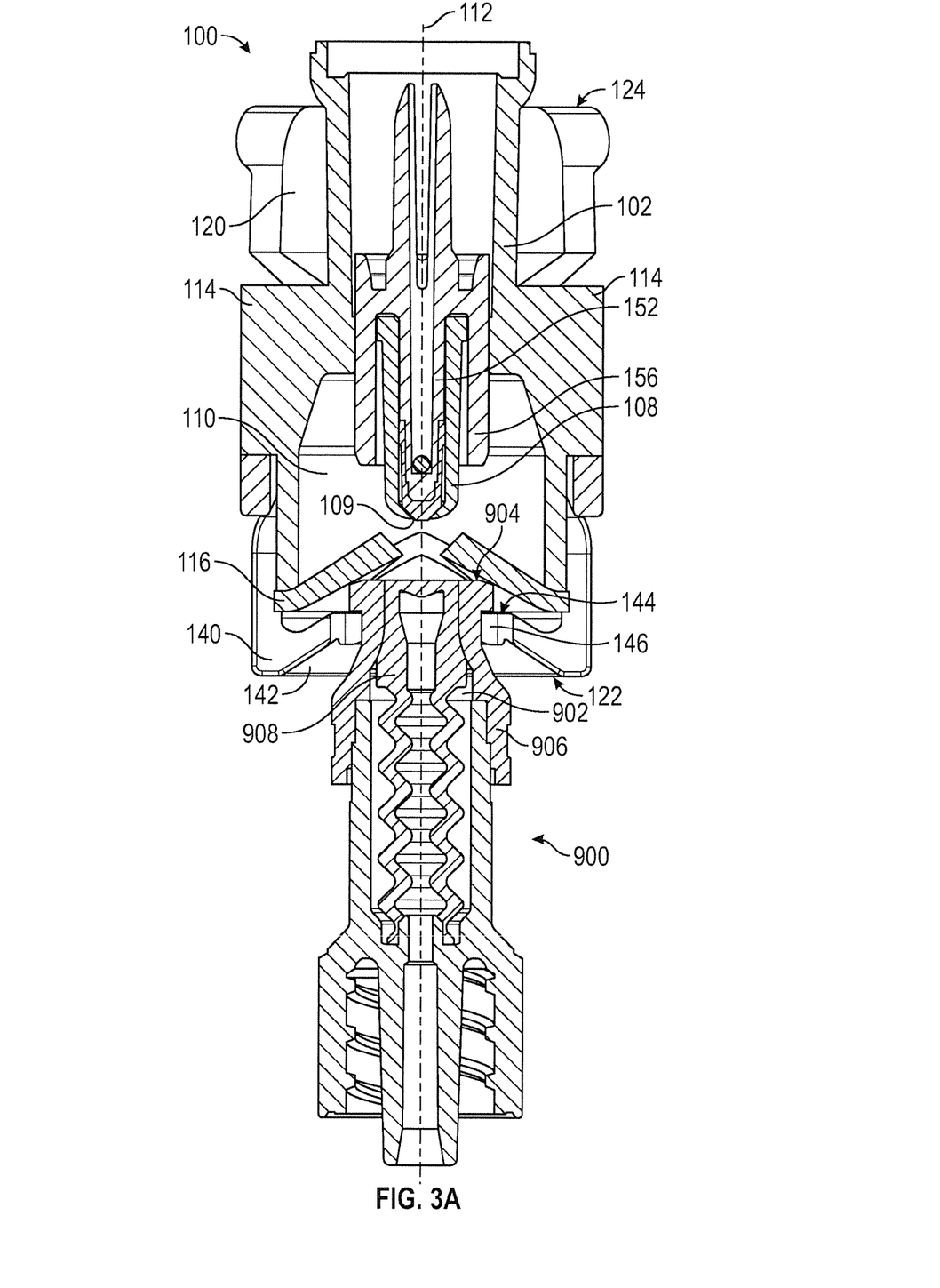
FIG. 3A illustrates a sectional view of the medical connector of FIG. 2 in a closed position, illustrating the relationship between the luer portion of the medical connector and a reciprocal connector.
Figure 3B:
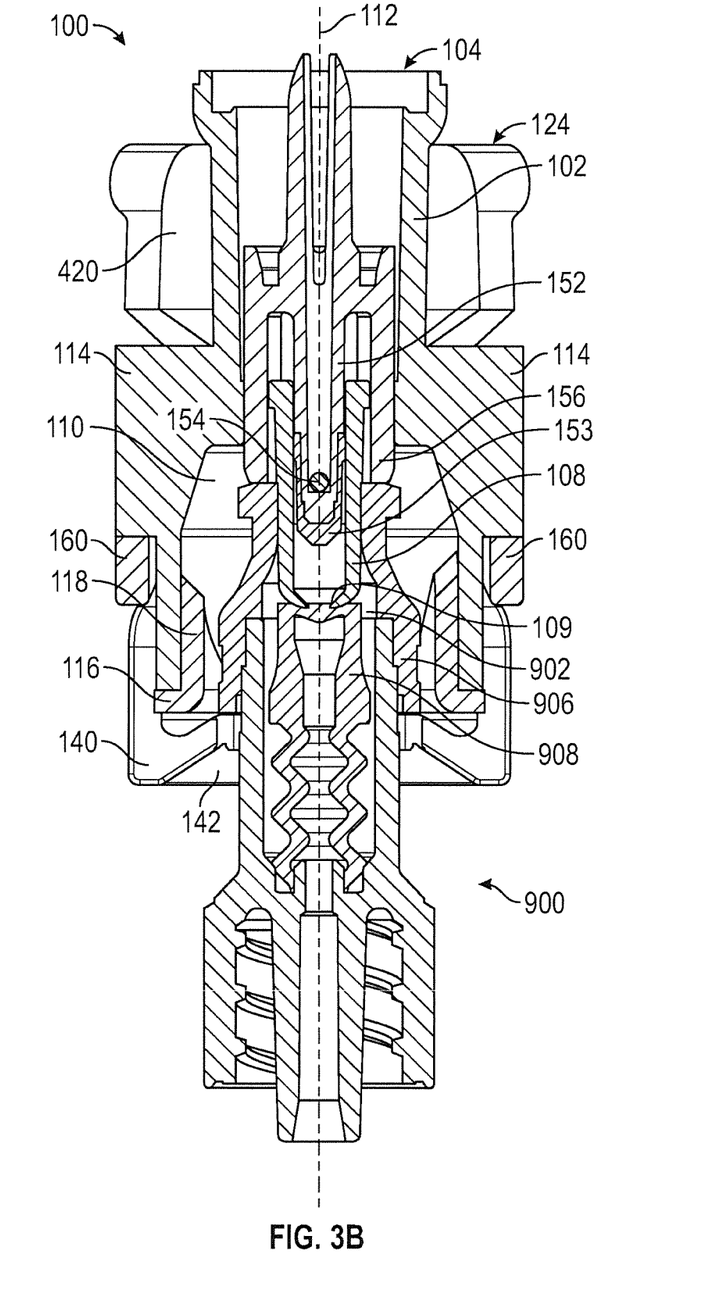
FIG. 3B illustrates a sectional view of the medical connector of FIG. 2 in an open position, illustrating engagement between the medical connector and a reciprocal connector.

FIGS. 3A-3B illustrate embodiments of medical connector 100 in relation to a reciprocal connector 900. The reciprocal connector 900 includes a mating luer 902. The mating luer 902 includes a top surface 904 and a ridge 906. The ridge 906 may include a circumferentially outward extending portion, a thread on an outside surface, or a segment of the reciprocal connector 900 comprising an increased cross-sectional width. In an embodiment, the mating luer 902 is a female luer configured to receive the luer portion 108 of the medical connector 100.

Referring to FIG. 3A, the post 152 extends through the fluid path in the luer portion 108 when the medical connector 100 is in a closed position. In the closed position, the closed end of post 152 seals the open tip 109 of the luer portion 108 thereby closing the fluid path. In some embodiments, barbs 156 are connected to the post 152 and extend along an exterior of the luer portion 108 toward the outlet port 106.

In an open position, illustrated in FIG. 3B, the medical connector 100 is coupled to the reciprocal connector 900 such that the luer portion 108 engages with the mating luer 902. To place the medical connector 100 in the open position, the outlet port 106 of the medical connector 100 and the top surface 904 of the reciprocal connector 900 are aligned along axis 112 as illustrated in FIG. 3A. When at least one of the medical connector 100 or reciprocal connector 900 is moved toward the other, the top surface 904 is permitted to pass beyond the apex area 146 of the latch member 140. As the top surface 904 passes beyond the apex area 146 of the latch member 140, the flaps 118 of the seal 116 are displaced into the cavity 110. As the reciprocal connector 900 further enters the cavity 110 of the medical connector 100, the ridge 906 having a cross-sectional width that is greater than the cross-sectional width between the apex areas 146, engages the ramp surface 142 thereby urging the first end 122 and 132 of each arm 120 and 130 away from the axis 112. When the reciprocal connector 900 is inserted into the cavity 110 to such an extent that the apex area 146 is beyond the ridge 906, the first end 122 and 132 of each arm 120 and 130 is permitted to return toward the axis 112 such that the engagement surface 144 is adjacent to the ridge 906 as illustrated in FIG. 3B.

Still referring to FIG. 3B, the luer portion 108 of the medical connector 100 extends through the top surface 904 into the mating luer 902 to displace a flexible valve 908. The barbs 156 and post 152 are forced away from the tip 109 of the luer portion 108 by the top surface 904. In the open position, the closed end of post 152 is displaced from the tip 109 of the luer portion 108, thereby permitting flow between the tip 109 of the luer portion 108 and the lumen of the post 152 through the passage 154.

In the open position, movement of the reciprocal connector 900 in the opposite direction, away from the inlet port 104, is restricted by the engagement surface 144. The medical connector 100 and reciprocal connector 900 are decoupled by urging the second ends 124 and 134 of each arm toward the axis 112, thereby causing the first ends 122 and 132 and latch member 140 of each arm to move away from the axis 112. When first ends 122 and 132 and latch members 140 are moved away from the axis 112 such that the cross-sectional width between the apex areas 146 is greater than the cross-sectional width of the ridge 906, the medical connector 100 may be moved axially away and the reciprocal connector 900 withdrawn from the cavity 110.

Figure 4A:
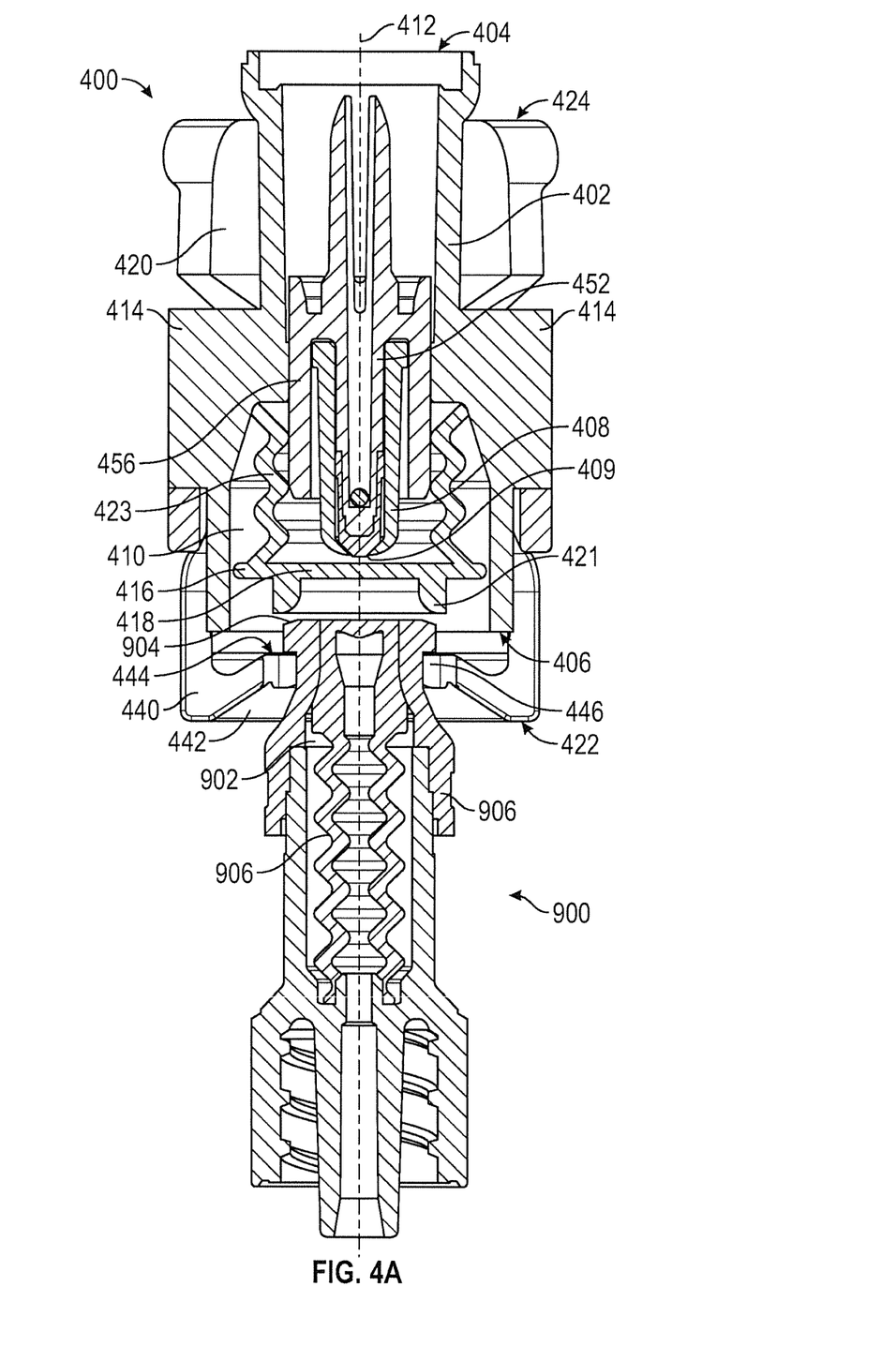
FIG. 4A illustrates a sectional view of an embodiment of a medical connector in a closed position accordance with aspects of the present disclosure, illustrating the relationship between the luer portion of the medical connector and a reciprocal connector.
Figure 4B:
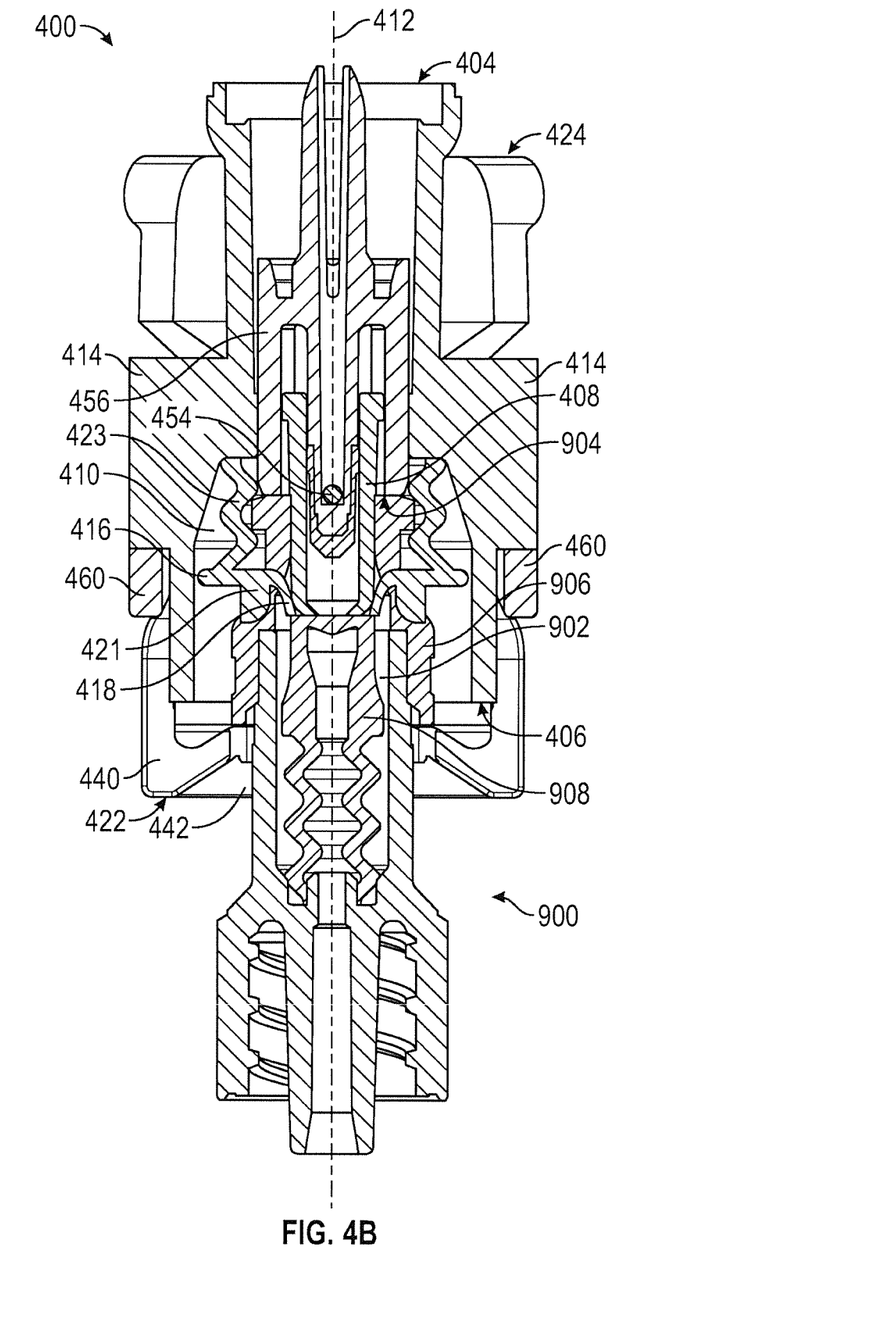
FIG. 4B illustrates a sectional view of the medical connector of FIG. 4A in an open position, illustrating engagement between the medical connector and a reciprocal connector.

FIGS. 4A-4B illustrate an embodiment of the medical connector 400 comprising a body 402 having an inlet port 404, an outlet port 406, and a first arm 420 coupled to the body 402. A seal 416 is disposed within a cavity 410 defined by the body 402. In some embodiments, the seal 416 is a cylinder disposed around an axis 412 between the inlet port 404 and outlet port 406. The seal 416 includes a base having a bellows portion 423 and an opposing head having an interface 421. The bellows portion 423 allows the seal 416 to compress or expand along the axis 412. In some embodiments, the interface 421 is a ring disposed circumferentially around the axis 412 and extending from the head toward the outlet port 406. Flaps 418 extend laterally inward from the interface 421 of the head toward the axis 412. The interface 421 engages with a top surface 904 of a reciprocal connector 900 to distribute the force of the reciprocal connector 900 to the bellows portion 423 and flaps 418 of the seal 416. In the closed position, illustrated in FIG. 4A, the bellows portion 423 is in an expanded state and the flaps are extended toward the axis 412 such that the luer portion 408 is enveloped by the seal 416.

To place the medical connector 400 in the open position, the outlet port 406 of the medical connector 400 and the top surface 904 of the reciprocal connector 900 are aligned along axis 412 as illustrated in FIG. 4A. When at least one of the medical connector 400 or reciprocal connector 900 is moved toward the other, the top surface 904 is permitted to pass beyond the apex area 446 of the latch member 440. When the top surface 904 passes beyond the apex area 446 of the latch member 440, the top surface 904 engages the interface 421. Further movement of the top surface 904 toward the inlet port 404 causes the bellows portion 423 of the seal 416 to axially compress. As the seal 416 is axially compressed, the flaps 418 engage the tip 409 of the luer portion 408. Further axial compression of the seal 416 forces the flaps 418 to become displaced toward the outlet port 406 as illustrated in FIG. 4B.

While the medical connector 400 and reciprocal connector 900 are being moved together such that the top surface 904 of the reciprocal connector 900 is axially compressing the seal 416, the ridge 906 having a cross-sectional width that is greater than the cross-sectional width between the apex areas 446, engages the ramp surface 442 thereby urging the first end 422 of the first arm 420 away from the axis 412. When the reciprocal connector 900 is inserted into the cavity 410 to such an extent that the apex area 446 is beyond the ridge 906, the first end 422 of the first arm 420 is permitted to return toward the axis 412 such that the engagement surface 444 is adjacent to the ridge 906.

Still referring to FIG. 4B, the luer portion 408 of the medical connector 400 extends through the top surface 904 into the mating luer 902 to displace a flexible valve 908, and the barbs 456 and post 452 are forced away from the tip 409 of the luer portion 408. In the open position, the closed end of post 452 is displaced from the tip 409 of the luer portion 408, thereby permitting flow between the tip 409 of the luer portion 408 and the lumen of the post 452 through the passage 454.

In the closed position, movement of the reciprocal connector 900 in the opposite direction, away from the inlet port 404, is restricted by the engagement surface 444. The medical connector 400 and reciprocal connector 900 are decoupled by urging the second ends of each arm toward the axis 412, thereby causing the first ends and the latch member 440 of each arm to move away from the axis 412. When first ends are moved away from the axis 412 such that the cross-sectional width between the apex areas 446 is greater than the cross-sectional width of the ridge 906, the medical connector 400 may be moved axially away from the top surface and decoupled from the reciprocal connector 900.

Figure 5:
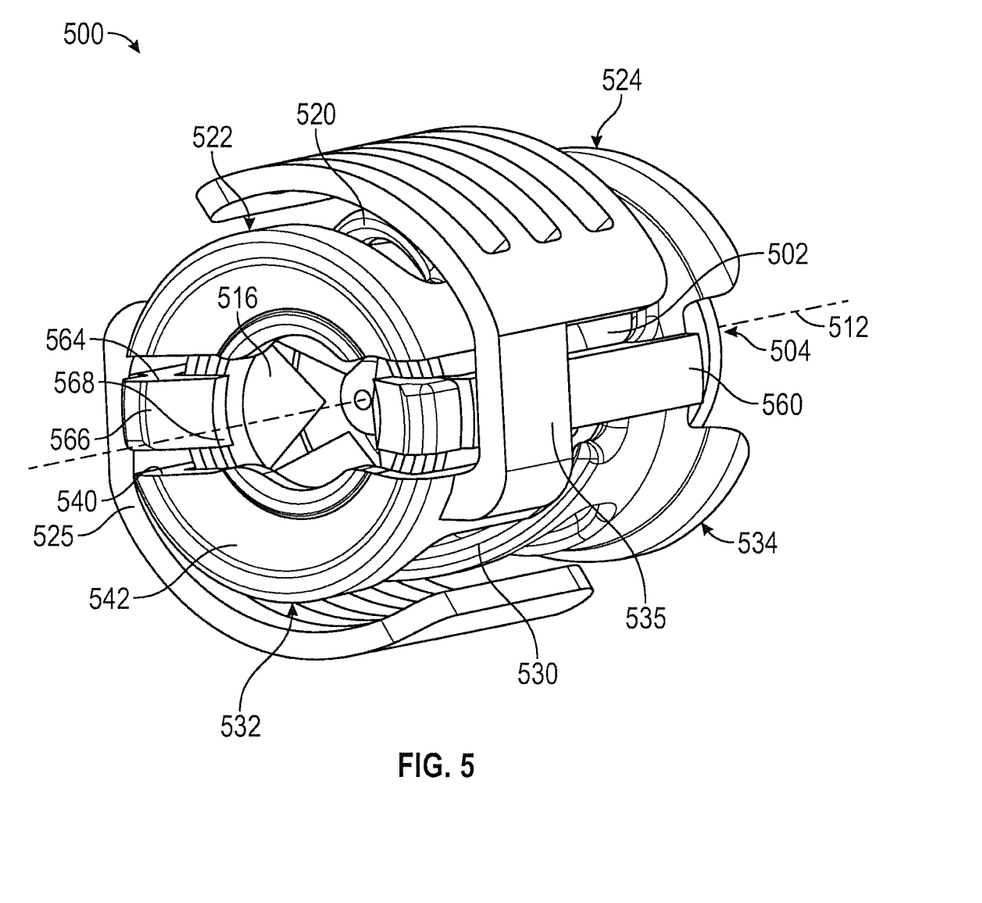
FIG. 5 illustrates a perspective view of an embodiment of a medical connector in accordance with aspects of the present disclosure.
Figure 6:
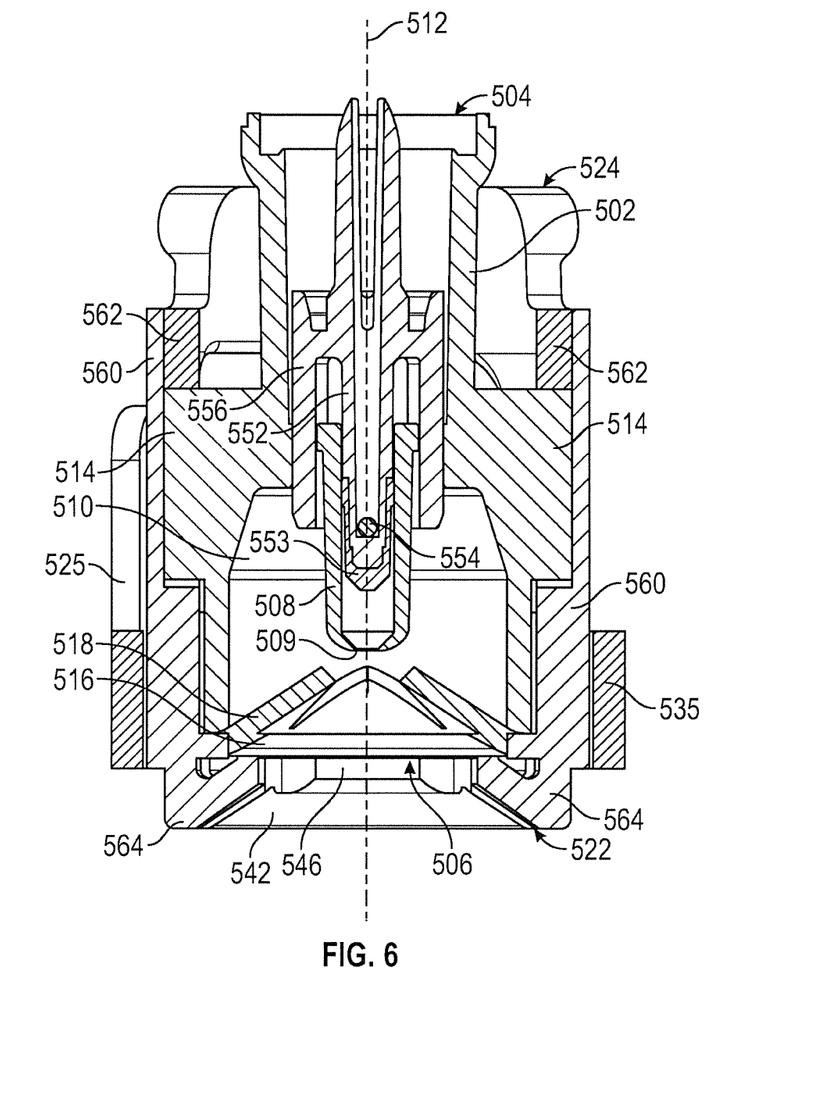
FIG. 6 a sectional view of the medical connector of FIG. 5.

Referring to FIGS. 5-6, an embodiment of a medical connector 500 is illustrated. The medical connector 500 comprises a body 502 having an inlet port 504 and an output port 506. The body 502 defines a cavity 510 and a male luer portion 508 extending toward the outlet port 506 and into the cavity 510. A fluid path between the inlet port 504 and outlet port 506 is defined by the body 502, the male luer portion 508, and cavity 510. Further, an axis 512 is defined between the inlet port 504 and outlet port 506. A protrusion 514 extends from an exterior surface of the body 502. The protrusion 514 is located between the inlet port 504 and the outlet port 506. In some embodiments, the protrusion 514 extends from the body 502 on opposing sides of the axis 512, and includes an elongated tab, groove, ridge, dimple, or aperture.

A first arm 520 comprises a first end 522 and an opposing second end 524. The first arm 520 is coupled to the body 502 coaxially with the axis 512 such that the first end 522 is adjacent to the outlet port 506, and the second end 524 is adjacent to the inlet port 504. A second arm 530 is also coupled to the body 502 coaxially with the axis 512 such that the first end 532 is adjacent to the outlet port 506, and the second end 534 is adjacent to the inlet port 504. Each of the first arm 520 and the second arm 530 are shaped as an arch around the axis 512 and extend around a portion of the body 502 toward each protrusion 514. In some embodiments, the arm 520 and 530 are unitarily formed with the body 502, for example by machining or casting. In the embodiment, the first arm 520 and the second arm 530 are pivotably coupled to the body 502.

In an embodiment, each arm 520 and 530 is coupled together by a bridge 560 extending between each arm 520 and 530. In some embodiments, a bridge 560 includes a tab, groove, ridge, dimple, or aperture configured to mate with a protrusion 514 on the body 502. In some embodiments, each bridge 560 defines an elongated slit 562 along an inside surface partially toward the outlet port 506. The first arm 520 and the second arm 530 are coupled to the body 502 by inserting the body 502 between the first arm 520 and the second arm 530 with the outlet port 506 directed toward the first ends 522 and 532. In this direction, the protrusions 514 enter the elongated slit 562 of each bridge 560 to couple each arm 520 and 532 with the body 502.

In some aspects, the bridge 560 includes a protrusion extending toward the body 502. The protrusion may be configured to mate with a recess in the body 502. The cross-sectional width between a tip of the protrusions extending from each bridge 560 may be less than the cross-sectional width of the outer surface of the body 502. The first arm 520 and the second arm 530 are coupled to the body 502 by inserting the body 502 between the first arm 520 and the second arm 530 with the outlet port 506 directed toward the first ends 522 and 532. As the body 502 is advanced between the protrusions, the bridge 560 between each arm 520 and 530 is biased away from the axis 512. Once the each protrusion aligns with a respective recess in the body 502, each bridge 560 is permitted to return toward the axis 512 such that the protrusion is received within the recess to couple each arm 520 and 530 with the body 502.

In some embodiments, the bridge 560 extends beyond the outlet port 506 and terminates in a guide 564 disposed between the latch member 540 of the first arm 520 and the second arm 530. The guide 564 includes a ramp surface 566 extending partially toward the axis 512 and an apex area 568. The cross-sectional width between each apex area 568 is greater than or equal to the outer surface of a mating luer 902 portion of a reciprocal connector 900. The ramp surface 566 of each guide 564 directs the top surface 904 of the reciprocal connector 900 into alignment with axis 512. The cross-sectional width between apex areas 568 permits a top surface 904 and a ridge 906 of the reciprocal connector 900 to pass beyond the apex area 568 of each latch member 540.

The first end 522 of the first arm 520 and the first end 532 of the second arm 530, each comprise a latch member 540 that extends laterally inward from an edge of the first end 522 and 532 toward the axis 512. Each latch member 540 comprises a ramp surface 542, an engagement surface 544, and an apex area 546. Each of the ramp surface 542 and the engagement surface 544 extend transversely to each other. The apex area 546 is disposed at the interface between the ramp surface 542 and the engagement surface 544.

In an embodiment, each arm 520 and 530 comprises an extension 525 and 535, respectively. For clarity and brevity, the following explanation is directed to the first arm 520. However, in an embodiment, each arm comprises complimentary features. With reference to the first arm 520, the extension 525 is coupled between the first end 522 and the protrusion 514. The extension 525 extends from the first end 522 beyond the axis 512 such that movement of the extension 525 toward the axis 512 urges the first end 522 away from the axis 512. In an embodiment, the extension 525 extends over the bridge 560 and comprises an arc over at least a portion of the second arm 530.

A seal 516 is coupled to the body 502. In an embodiment, the seal 516 is coupled to the outlet port 506 of the body 502 and includes a flap 518 that extends from an edge of the outlet port 506 toward the axis 512. In some embodiments, the seal 516 includes one or more flaps 518 that extend laterally inward from an edge of the outlet port 506. In some embodiments, a seal comprising a bellows portion surrounds the luer portion 508 and includes flaps extending from an opening toward the axis 512 to envelop the luer portion 508 within the cavity 510.

A post 552 extends through the fluid path in the luer portion 508. The post 552 defines a lumen having an open end, an opposing closed end, and a passage 554 through a sidewall between the open end and the closed end. When the medical connector 500 is in a closed position, the closed end of post 552 seals the open tip 509 of the luer portion 508 thereby closing the fluid path. In some embodiments, the post 552 includes a seal 553 on the outside surface of the closed end to prevent fluid flow through the open tip 509 of the luer portion 508 when the medical connector 500 is in a closed position.

When the medical connector 500 is coupled with a reciprocal connector 900 in an open position, the luer portion 508 engages with the mating luer 902. To place the medical connector 100 in the open position, the outlet port 506 of the medical connector 500 and the top surface 904 of the reciprocal connector 900 are aligned along the axis 512. When at least one of the medical connector 500 or reciprocal connector 900 is moved toward the other, the ramp surface 566 of each guide 564 directs the top surface 904 of the reciprocal connector 900 into alignment with axis 512. The cross-sectional width between the apex areas 546 of each latch member 540 permits the top surface 904 and ridge 906 of the reciprocal connector 900 to pass beyond the apex area 546. As the reciprocal connector 900 further enters the cavity 510 of the medical connector 500, the ridge 906 having a cross-sectional width that is greater than the cross-sectional width between the apex areas 546, engages the ramp surface 542 thereby urging the first end 522 and 532 of each arm 520 and 530 away from the axis 512. When the reciprocal connector 900 is inserted into the cavity 510 to such an extent that the ridge 906 is beyond the apex areas 546, the first end 522 and 532 of each arm 520 and 530 is permitted to return toward the axis 512 such that the engagement surface 544 is adjacent to the ridge 906.

In the open position, the closed end of post 552 is displaced from the tip 509 of the luer portion 508, thereby permitting flow between the tip 509 of the luer portion 508 and the lumen of the post 552 through the passage 554.

In the open position, movement of the reciprocal connector 900 in the opposite direction, away from the inlet port 504, is restricted by the engagement surface 544 of each latch member 540 against the ridge 906 of the reciprocal connector 900. The medical connector 500 and reciprocal connector 900 are decoupled by urging the extensions 525 and 535 of each arm toward the axis 512, thereby causing the first ends 522 and 532 and latch members 540 of each arm 520 and 530 to move away from the axis 512. When first ends 522 and 532 are moved away from the axis 512 such that the cross-sectional width between the apex areas 546 is greater than the cross-sectional width of the ridge 906, the medical connector 500 may be moved axially away and the reciprocal connector 900 withdrawn from the cavity 510.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim. The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." The term "some" refers to one or more. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A medical connector comprising:
   a body having an inlet port, defining a proximal-most end, an outlet port defining a distal-most end, a cavity that extends from the outlet port toward the inlet port, a luer taper that extends into the cavity toward the outlet port, a fluid path from the inlet port through the luer taper to the outlet port;
   a seal coupled to a circumferential edge of the outlet port and extending laterally inward from the circumferential edge of the outlet port toward the luer taper to at least partially enclose the cavity; and
   a first arm, a second arm, and a bridge that extends between the first and second arms, wherein an outer surface of the body comprises any of a protrusion or a slot, and the bridge comprises the other of the protrusion or the slot, such that the protrusion is positioned within the slot to pivotably couple the first and second arms to the body, and wherein the first and second arms are configured to engage against a reciprocal connector to resist movement of the reciprocal connector relative to the body.

2. The medical connector of claim 1, wherein the any of the first and second arms comprises a latch member extending from the arm toward the body.

3. The medical connector of claim 2, wherein the latch member comprises a ramp surface, an engagement surface extending transversely to the ramp surface, and an apex area that transitions between the ramp surface and the engagement surface.

4. The medical connector of claim 1, wherein the any of the first and second arms comprise a first end and an opposing second end, and wherein, when the first end of the arm moves away from the body, the second end of the arm is urged toward the body.

5. The medical connector of claim 1, wherein the seal comprises at least one flap extending from the circumferential edge of the outlet port.

6. The medical connector of claim 5, wherein a length of the at least one flap from the circumferential edge of the outlet port is less than a distance between the circumferential edge of the outlet port and the luer taper, such that the at least one flap is free from the luer taper when the at least one flap is displaced into the body.

7. The medical connector of claim 1, wherein the protrusion and the slot are positioned between the inlet port and the outlet port.

8. The medical connector of claim 7, wherein an extension is coupled to the any of the first and second arms between a first end of the arm and the protrusion such that when the extension is urged toward the body, the first end is urged away from the body.

9. The medical connector of claim 1, wherein the bridge comprises a guide portion extending toward the distal-most end, the guide portion comprising a ramp surface extending toward the outlet port.

10. A medical connector comprising:
a body having an inlet port, an outlet port, a cavity that extends from the outlet port toward the inlet port, a luer taper that extends into the cavity, a fluid path from the inlet port through the luer taper to the outlet port, and a protrusion that extends from an outer surface of the body; and
a first arm and a second arm, pivotably coupled to the body and a bridge therebetween, the bridge comprising an elongated slit extending through the bridge partially toward the outlet port, and configured to receive the protrusion within the elongated slit.

11. The medical connector of claim 10, further comprising a seal coupled to the body at the outlet port, wherein the seal extends from the outlet port toward the luer taper.

12. The medical connector of claim 11, wherein the seal comprises at least one flap extending from the outlet port, the flap having a length between the outlet port toward the luer taper, wherein the length is less than a distance between the outlet port and the luer taper, such that the flap is free from the luer taper when the flap is displaced into the body.

13. The medical connector of claim 10, wherein any of the first and second arms comprise a latch member extending from the respective arm toward the body.

14. The medical connector of claim 13, wherein the latch member comprises a ramp surface, an engagement surface extending transversely to the ramp surface, and an apex area that transitions between the ramp surface and the engagement surface.

15. The medical connector of claim 10, wherein a first extension is coupled to the first arm, between a first end of the first arm and the protrusion such that when the first extension is urged toward the body, the first end is urged away from the body.

16. The medical connector of claim 10, wherein a second extension is coupled to the second arm, between a first end of the second arm and the protrusion such that when the second extension is urged toward the body, the first end is urged away from the body.

17. The medical connector of claim 10, wherein the first and second arms are configured to engage against a reciprocal connector to resist movement of the reciprocal connector relative to the body.

* * * * *